United States Patent [19]
Tanaka et al.

[11] Patent Number: 5,895,820
[45] Date of Patent: Apr. 20, 1999

[54] PROCESS FOR THE PRODUCTION OF TRIMELLITIC ACID AND PROCESS FOR THE PRODUCTION OF TRIMELLITIC ACID ANHYDRIDE

[75] Inventors: Kazuo Tanaka; Masashi Yabuno; Hiroshi Ogawa; Atsushi Ohkoshi, all of Kurashiki, Japan

[73] Assignee: Mitsubishi Gas Chemical Company, Inc., Japan

[21] Appl. No.: 09/115,993

[22] Filed: Jul. 15, 1998

[30] Foreign Application Priority Data

| | | | |
|---|---|---|---|
| Jul. 16, 1997 | [JP] | Japan | 9-191272 |
| Jul. 16, 1997 | [JP] | Japan | 9-191273 |
| Sep. 19, 1997 | [JP] | Japan | 9-255177 |
| May 27, 1998 | [JP] | Japan | 10-145843 |

[51] Int. Cl.$^6$ .................................. C07C 51/265
[52] U.S. Cl. ..................... 549/245; 562/414; 562/416; 562/487
[58] Field of Search .................... 562/414, 416, 562/487; 549/245

[56] References Cited

U.S. PATENT DOCUMENTS

| | | | |
|---|---|---|---|
| 5,124,461 | 6/1992 | Park | 549/245 |
| 5,250,724 | 10/1993 | Fumagalli et al. | 562/416 |

*Primary Examiner*—Samuel Barts
*Attorney, Agent, or Firm*—Wenderoth, Lind & Ponack, L.L.P.

[57] ABSTRACT

A process for the production of a trimellitic acid by oxidizing dialkyl aromatic aldehyde and/or its oxide derivative in a liquid phase, the oxidation being carried out in a lower aliphatic carboxylic acid solvent having a water content of 5 to 70% by weight in the presence of a catalyst containing a heavy metal and bromine or being carried out in a solvent containing a lower aliphatic carboxylic acid in the presence of a bromine-manganese catalyst system containing zirconium and/or cerium, and a process for the production of high-quality trimellitic acid anhydride from the trimellitic acid.

19 Claims, 1 Drawing Sheet

PROCESS FOR THE PRODUCTION OF TRIMELLITIC ACID AND PROCESS FOR THE PRODUCTION OF TRIMELLITIC ACID ANHYDRIDE

BACKGROUND OF THE INVENTION

1. Field of the Invention

The present invention relates to a process for the production of a trimellitic acid by oxidizing dialkyl aromatic aldehyde and/or its oxide derivative in a liquid phase, and a process for the production of high-quality trimellitic acid anhydride from the trimellitic acid.

2. Description of the Prior Art

Conventionally, aromatic polycarboxylic acid have been produced by oxidation of polyalkylbenzene, and trimellitic acid from pseudocumene, trimesic acid from mesitylene, pyromellitic acid from durene and mellophanic acid from isodurene are known. For example, JP-A-6-16655 discloses a process for the production of trimellitic acid by oxidizing pseudocumene in a liquid phase, in which the oxidation is carried out in the presence of cerium, cobalt and manganese and optionally in the co-presence of zirconium and a bromine catalyst and cerium and bromine are allowed to react in a second oxidation step by a batch method. However, since the above catalyst system is complicated, and further, since the reaction method is complicated, it is difficult to recover and recycle the catalysts.

In the oxidation of alkylbenzenes to corresponding aromatic polycarboxylic acids, the alkylbenzenes differ from one another in reactivity depending upon the position of substituted methyl group. Trimellitic acid or pyromellitic acid formed from pseudocumene or durene has a structure in which one carboxylic acid is positioned in o-position to the other, and therefore, a heavy metal catalyst is decreased in activity and the yield from the oxidation decreases as compared with polymethylbenzene having such a structure. Various proposals have been therefore made for the improvement of a catalyst system. Yields from the oxidation are improved, while it is difficult to recover and recycle catalysts since the catalyst system is complicated.

On the other hand, it is known that an aromatic aldehyde is formed by converting an aromatic hydrocarbon to a formyl compound and used as a raw material for producing an aromatic polycarboxylic acid. For example, JP-B-58-2222 discloses a method in which an aromatic aldehyde is oxidized in a water solvent to continuously produce an aromatic polycarboxylic acid. This method requires a special reactor material formed of zirconium due to a high bromine concentration.

Further, JP-A-57-38745 discloses a method in which a polyalkyl aromatic aldehyde is oxidized in the presence of cobalt, manganese and bromine in a acetic acid solvent, to produce an aromatic polycarboxylic acid.

Plastic industries use trimellitic acid as an intermediate for the synthesis of a resin or a plasticizer. In many cases, trimellitic acid is converted to trimellitic acid anhydride by dehydration, and in particular, it is used as an intermediate for the production of a polyester. It is therefore strongly desired to supply an inexpensive trimellitic acid.

The present inventors have studied the production of trimellitic acid by oxidizing a dialkyl aromatic aldehyde in the presence of cobalt, manganese and bromine in an acetic acid solvent according to the method of the above JP-A-57-38745, and have found the following. It is difficult to recover and recycle the catalysts due to a large metal content in a crystal, and it is also required to add improvements in view of yields.

It is a first object of the present invention to provide a process for the production of trimellitic acid, which does not require any special reactor material for continuously oxidizing a dialkyl aromatic aldehyde and/or its oxide derivative, which permits the recycle of a catalyst and which provides high yields.

In a method using a catalyst system of cobalt, manganese and bromine like JP-A-57-38745, it is desired to improve the reaction rate and the yield.

It is a second object of the present invention to provide a process for the continuous and advantageous production of trimellitic acid from a dialkyl aromatic aldehyde and/or its oxide derivative as raw material in the presence of a highly active catalyst developed in place of the catalyst system of cobalt, manganese and bromine.

Trimellitic acid is an aromatic tri-basic acid and is essential as a raw material for a high-grade plasticizer or a heat-resistant plastic. A plasticizer or a plastic requires a less-colored high-purity trimellitic acid anhydride as a raw material therefor.

As described in JP-B-58-2222 and JP-A-61-280448, trimellitic acid anhydride is produced from crude trimellitic acid obtained by oxidizing pseudocumene, dimethylbenzaldehyde or its oxide intermediate with molecular oxygen in the presence of bromide ion or in the presence of bromide ion and heavy metal ion as a catalyst.

Trimellitic acid anhydride is produced by thermally dehydrating crude trimellitic acid at 220 to 230° C. and distilling the resultant trimellitic acid anhydride under reduced pressure, as is described in Ullman's literature ("Encyclopedia of Industrial Chemistry", 4th ed. vol. 9, page 150).

However, the trimellitic acid anhydride produced by the above method is not necessarily satisfactory in hue and purity, and it is desired to supply trimellitic acid anhydride having a higher quality as a raw material for a high-grade plasticizer or heat-resistant plastic in recent years.

JP-B-47-35421 discloses a method in which trimellitic acid is treated with boric acid. Further, For an improvement of this method, Japanese PCT Publication No. 4-501271 discloses a method in which at least 0.1% by weight of boron is added to a trimellitic acid anhydride, the mixture is thermally treated and the treated trimellitic acid anhydride is distilled for improving its hue.

However, the trimellitic acid anhydride produced by the above method is not yet necessarily satisfactory in hue and purity, and it is further desired to supply trimellitic acid anhydride having a much higher quality as a raw material for a high-grade plasticizer or heat-resistant plastic in recent years.

Further, when pseudocumene or dimethylbenzaldehyde as a raw material contains impurities which cannot be converted to trimellitic acid by oxidation, the resultant trimellitic acid anhydride is degraded in hue and purity in some cases, and it is therefore desired to develop a method of producing trimellitic acid anhydride free of an influence caused by the raw material.

It is a third object of the present invention to provide a process for the industrially advantageous production of a high-quality trimellitic acid anhydride from a crude trimellitic acid having a low purity and containing coloring substances, obtained by the oxidation of pseudocumene or dimethylbenzaldehyde.

SUMMARY OF THE INVENTION

The present inventors have made diligent studies for overcoming the above problems involved in the production of trimellitic acid, and as a result, the following has been found. In the oxidation of dialkylaldehyde and/or its oxide derivative, the water concentration in a solvent is adjusted to a specific range, whereby the concentration of metals contained in a crystal is remarkably low, the catalyst can be therefore recycled and the yield of trimellitic acid is also improved. On the basis of the above finding, they have arrived at the present invention 1.

That is, the present invention 1 provides a process for the production of trimellitic acid, which comprises oxidizing a dialkyl aromatic aldehyde and/or its oxide derivative at 180 to 240° C. with an oxygen-containing gas in a lower aliphatic carboxylic acid solvent having a water content of 5 to 70% by weight in the presence of a catalyst containing a heavy metal and bromine.

Further, the present inventors have found that a zirconium-manganese-bromine catalyst, a cerium-manganese-bromine catalyst and a zirconium-cerium-manganese-bromine catalyst have higher activity than a cobalt-manganese catalyst in the oxidation of dialkyl aromatic aldehyde and/or its oxide derivative, and have arrived at the present invention 2.

That is, the present invention 2 provides a process for the production of trimellitic acid, which comprises oxidizing a dialkyl aromatic aldehyde and/or its oxide derivative in a liquid phase at a temperature between 180° C. and 240° C. in a solvent containing a lower aliphatic carboxylic acid in the presence of a bromine-manganese catalyst system containing zirconium and/or cerium.

Further, the present inventors have made diligent studies for overcoming the poor hue in the properties of trimellitic acid anhydride, and as a result, the following has been found. In the method of Japanese PCT Publication No. 4-501271 for improving the hue of trimellitic acid anhydride, an oxide of boron added is concentrated in a distillation column bottom during the distillation, the bottom liquid is caused to have a high boiling point, the bottom temperature is raised and the viscosity of a residue is caused to increase. As a result, industrially, the distillation is difficult.

In contrast, trimellitic acid anhydride is distilled and separated with circulating a liquid in the distillation column bottom to a thermal treatment step, i.e., a thermal treatment vessel, whereby the higher boiling point of the distillation column bottom liquid can be avoided. Further, crude trimellitic acid or a mixture of trimellitic acid and trimellitic acid anhydride is thermally treated under reduced pressure in the presence of a boron oxide in the smallest amount that is necessary, and then the oxidation product is distilled, whereby trimellitic acid anhydride having a high quality can be stably and advantageously produced from a trimellitic acid raw material having a low purity. As a result, they have arrived at the present invention 3.

That is, the present invention 3 provides a process for the production of trimellitic acid anhydride from trimellitic acid obtained by oxidation of 1,2,4-aliphatic-groups-substituted benzene, dialkylbenzaldehyde and/or its oxide intermediate, which process comprises thermally treating trimellitic acid or a mixture of trimellitic acid with trimellitic acid anhydride, obtained by dehydration of trimellitic acid under heat, together with boron oxide under reduced pressure, then introducing a thermally treated product into a distillation column, and continuously recycling part of a bottom liquid in the distillation column to the step of the thermal treatment.

In the heat-treatment together with boron in the present invention 3, preferably, a boron oxide in an amount of 50 to 900 ppm based on the trimellitic acid or the mixture of trimellitic acid with trimellitic acid anhydride is added, the thermal treatment is carried out under a reduced pressure of 200 torr or less at a temperature of 250° C. for at least 5 minutes, and then the heat-treated product is introduced into a distillation column. Further, in the trimellitic acid and the trimellitic acid anhydride which are to be introduced into a distillation column, the content of the trimellitic acid based on the total amount of these is preferably 3% by weight or less.

Further, the present inventors have found the following trimellitic acid or a mixture of trimellitic acid with trimellitic acid anhydride, obtained by dehydration of trimellitic acid under heat, is thermally treated under reduced pressure for a long time without adding any oxide of boron, to decrease the content of trimellitic acid to 3% by weight or less, and then the distillation is carried out, whereby trimellitic acid anhydride having a high quality can be stably and advantageously produced from a trimellitic acid raw material having a low purity. As a result, they have arrived at the present invention 4.

That is, the present invention 4 provides a process for the production of trimellitic acid anhydride from crude trimellitic acid obtained by oxidation of 1,2,4-aliphatic-groups-substituted benzene, dialkylbenzaldehyde and/or its oxide intermediate, which process comprises thermally treating trimellitic acid or a mixture of trimellitic acid with trimellitic acid anhydride, obtained by dehydration of trimellitic acid under heat, until the amount of trimellitic acid based on the total amount of trimellitic acid and trimellitic acid anhydride is 3% by weight or less, and introducing the thermally treated product into a distillation column. In conditions of the thermal treatment, preferably, the reduced pressure is 200 torr or less, the temperature is at least 250° C. and the time period for the treatment is at least 30 minutes.

DETAILED DESCRIPTION OF THE INVENTION

Figure 1:
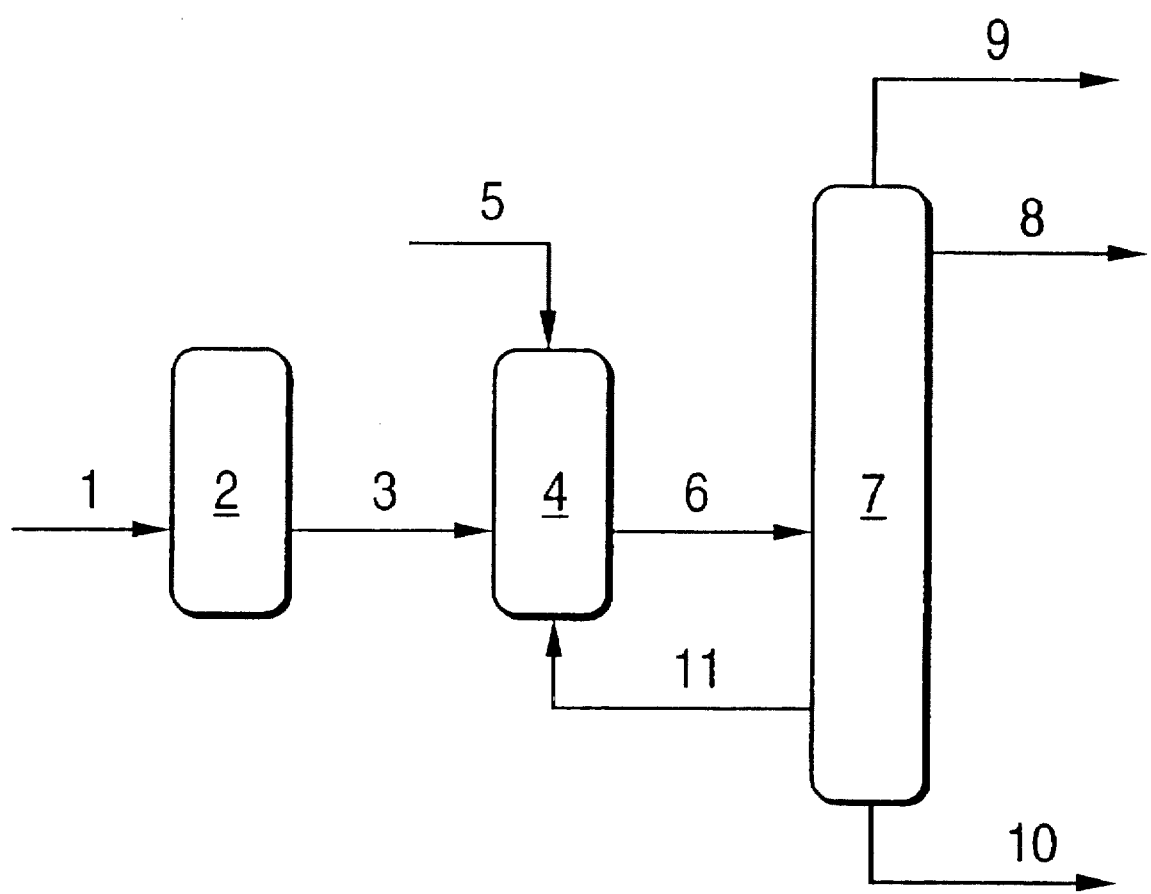
FIG. 1 shows an example of the flow of the process for the production of trimellitic acid anhydride, provided by the present invention 3.

The dialkyl aromatic aldehyde used in a raw material in the oxidation in the present inventions 1 and 2 includes 2,4-dimethylbenzaldehyde 2,5-dimethylbenzoic aldehyde and 3,4-dimethylbenzaldehyde. The oxide derivative thereof includes 2,4-dimethylbenzoic acid, 2,5-dimethylbenzoic acid, 3,4-dimethylbenzoic acid, formylmethylbenzoic acid and methylphthalic acid.

The lower aliphatic carboxylic acid used as a solvent in the above oxidation is an aliphatic monocarboxylic acid having 1 to 5 carbon atoms, and it can be selected from formic acid, acetic acid, propionic acid, butyric acid or mixtures of these. Acetic acid and propionic acid are preferred, and acetic acid is particularly preferred.

The water content in the solvent is 5 to 70% by weight, preferably 10 to 60% by weight. When the water content is lower than the above lower limit, a salt of trimellitic acid and heavy metal is liable to be formed, and the catalyst activity is therefore decreased. When the water content is higher than the above upper limit, the reaction rate decreases and the yield is therefore low.

The amount of the solvent to the amount of the dialkyl aromatic aldehyde and its oxide derivative is generally 1 to 20 times, preferably 3 to 10 times.

The oxidation in the present invention 1 uses heavy metal(s) as a catalyst, and manganese alone or manganese and cobalt are used as a catalyst. The oxidation in the present invention 2 uses, as a catalyst, a bromine-manganese based catalyst containing zirconium and/or cerium.

These manganese, cobalt, zirconium and cerium compounds include organic acid salts, halides and carbonates. In particular, it is preferred to use them in the form of acetate or bromide.

The bromine compound used as a catalyst for the oxidation is not specially limited so long as it is dissolved in the reaction system and generates bromide ion. The bromine compound includes inorganic bromides such as hydrogen bromide, sodium bromide and cobalt bromide, and organic bromides such as tetrabromoethane. In particular, hydrogen bromide, cobalt bromide and manganese bromide are preferred.

According to the present invention 2, zirconium or cerium is added to the manganese-bromide system catalyst. In this case, the catalyst activity is enhanced, and the reaction rate is greatly improved. It is particularly preferred to add both zirconium and cerium.

The concentration of the heavy metal(s) in the solvent is 0.03 to 2% by weight, preferably 0.05 to 1% by weight. When the catalyst concentration is lower than the above lower limit, the reaction does not proceed. When the catalyst concentration exceeds the above upper limit, the catalyst causes an adverse effect on the reaction. Manganese is generally used as a heavy metal, while cobalt may be used as part of the heavy metal.

When both zirconium and cerium are added to manganese, the heavy metal composition ratio is preferably as follows. On the basis of the total amount of the heavy metals, the content of zirconium is 1 to 10% by weight, the content of cerium is 1 to 20% by weight, and the content of manganese is 70 to 98% by weight.

The bromine concentration in the solvent is 0.05 to 2% by weight, preferably 0.1 to 1% by weight. When the bromine concentration is lower than the above lower limit, the reaction does not proceed. When the bromine concentration is higher than the above upper limit, severe corrosion takes place. The atomic ratio of the heavy metal catalyst to bromide ion is 0.5 to 10, preferably 0.8 to 5.

The oxygen-containing gas used for the oxidation include oxygen gas and a gas mixture of oxygen with inert gas such as nitrogen or argon. Air is the most generally used.

The oxidation reactor is selected from a stirring vessel or a foaming column, while a stirring vessel is preferred for sufficient stirring in a reactor. The reaction procedure is preferably according to a semi-batch method or a continuous method. In the semi-batch method, it is preferred to continue the supply of the oxygen-containing gas for 5 to 60 minutes after the termination of the feed of a raw material, for completing the oxidation. In the continuous method, it is preferred to provide a plurality of reactors in series for improving the reaction yield.

The temperature for the oxidation is 180 to 240° C., preferably 190 to 230° C. In the oxidation temperature outside the above range, by-products increase in amount, and the yield of trimellitic acid is low.

In the oxidation, the oxygen-containing gas is continuously supplied to the reactor, and gas after the reaction is continuously withdrawn such that the pressure is 5 to 40 kg/cm$^2$, preferably 10 to 30 kg/cm$^2$. The oxygen concentration in discharged gas from the reactor is 0.1 to 8% by volume, preferably 1 to 5% by volume.

The reactor is provided with a reflux condenser for condensing a large amount of solvent contained in the discharged gas and water generated by the oxidation. The condensed solvent and water are generally recycled to the reactor, while part of them is withdrawn from the reaction system for adjusting the water concentration in the reactor.

The residence time of the reaction liquid in the reactor is generally 0.5 to 5 hours. When a plurality of reactors are provided in series, the above residence time is a total of residence time periods in a plurality of the reactors.

A reaction mixture from the oxidation is cooled to a temperature approximately between 10° C. and 120° C., preferably to a temperature approximately 20° C. and 40° C., and an obtained crystal is separated from the reaction mixture by filtration or centrifugal separation. The separated crude crystal of trimellitic acid reslurry-washed or rinsed with water or hydrous acetic acid, to remove organic impurities, metals, etc., contained in the crystal.

The oxidation is preferably continuously carried out, and in the continuous method, a most part of a reaction mother liquor after the separation of the crystal of trimellitic acid from the oxidation mixture is recycled to the oxidation system. Part of the reaction mother liquor is distilled for removing formed water and the remainder is used as a solvent.

The trimellitic acid crystal obtained according to the present invention 1 has a very small content of heavy metals and has a very high purity, and therefore, trimellitic acid anhydride can be obtained by direct dehydration under heat without any special purification step.

That is, when the dialkyl aromatic aldehyde and/or its oxide derivative is/are oxidized in a lower aliphatic carboxylic acid solvent containing water in the specified range according to the present invention 1, a trimellitic acid crystal in which the heavy metal concentration is very low can be obtained at high yields. Therefore, a most part of the catalyst components containing heavy metal and bromine are contained in the mother liquor after the crystal is recovered, and the above mother liquor is recycled to the oxidation reactor, whereby the catalyst can be recycled.

In the process of the present invention, therefore, the cost of the catalyst for the production of trimellitic acid can be decreased, and further, the trimellitic acid can be easily purified. As a result, the cost for recovering the catalyst components as measures for the prevention of environmental pollution can be also decreased.

In the process according to the present invention 1, the concentration of bromine in the catalyst components can be decreased, and therefore, the reactor does not require a special material.

In the present invention 2, the manganese-bromine system catalyst containing one or both of zirconium and cerium has higher catalyst activity than a conventional cobalt-manganese-bromine system catalyst, and when the dialkyl aromatic aldehyde and/or its oxide derivative are/is oxidized in a lower aliphatic carboxylic acid solvent containing water in the specified range in the presence of the above catalyst, trimellitic acid can be continuously obtained at high yields.

The continuous production of trimellitic acid, which has been conventionally difficult, can be carried out according to the present invention, and the trimellitic acid is obtained at high yields and the amount of an intermediate formed is small. Trimellitic acid can be therefore remarkably advantageously produced in industry, and the present invention is highly significant in industry.

Trimellitic acid used for the purification in the present inventions 3 and 4 is produced by the oxidation of 1,2,4- aliphatic group substituted benzene, dialkylbenzaldehyde and their oxidation intermediates. Specific examples of the raw material for the oxidation include pseudocumene, 2,4-dialkylbenzaldehyde, 2,5-dialkylbenzaldehede, 3,4-dialkylbenzaldehyde and oxidation intermediates of these such as 2,4-dialkylbenzenecarboxylic acid, 2,5-dialkylbenzencarboxylic acid, 3,4-dialkylbenzenecarboxylic acid, etc. The raw material for the oxidation is not necessarily required to have a purity of 100%, and there may be used a raw material containing 5% or less of impurities which does not form trimellitic acid by oxidation.

Trimellitic acid can be obtained by oxidizing the above oxidation raw material with molecular or gaseous oxygen in the presence of a heavy metal oxidation catalyst such as manganese in a liquid phase oxidation of aliphatic-group-substituted benzene. More specifically, the above raw material such as pseudocumene or 2,4-dimethylbenzaldehyde is oxidized with molecular oxygen in water or a hydrous acetic acid solvent at a temperature approximately between 200° C. and 280° C. in the presence of a catalyst in which the heavy metal and bromine are co-present. The oxidation can be carried out by any one of a batch method, a semi-continuous method and a continuous method, while it is the most preferred in industry to employ the continuous oxidation method.

Trimellitic acid is obtained by the above liquid phase oxidation, while the present inventions 3 and 4 are preferably carried out by dehydration of crude trimellitic acid under heat before distillation such that the trimellitic acid content in a mixture of trimellitic acid with trimellitic acid anhydride is 3% by weight or less, preferably 0 to 1% by weight.

However, it is very difficult to increase the dehydration ratio of trimellitic acid from the crude trimellitic acid as described above when the dehydration is carried out in one vessel under slightly reduced pressure or atmospheric pressure. It is therefore preferred to divide a dehydration reactor to at least two stages and increase the dehydration ratio stepwise.

For example, in a first dehydration reactor, the thermal dehydration under heat is carried out at a temperature of 200 to 300° C. under atmospheric pressure or a reduced pressure causing no influence on the operation, and in a second dehydration reactor, the dehydration is carried out under a reduced pressure of 200 torr or less, preferably 100 torr or less, whereby the content of trimellitic acid which is not dehydrated is adjusted to 3% or less.

In the second dehydration reactor (thermal treatment vessel), the thermal treatment is also carried out at the same time, whereby a color component is converted to a component having a high boiling point. As conditions of converting the color component to a component having a high boiling point, it is required to carry out thermal treatment at 250° C. or higher for at least 5 minutes. The preferred temperature is in the range of from 250° C. to 300° C., and the higher the temperature is, the smaller the time period required for the thermal treatment is. However, when the temperature is higher than 300° C., the decomposition of trimellitic acid anhydride is no longer negligible. When the above thermal treatment is carried out under reduced pressure, the color component is converted to a component having a high boiling point, and it can be removed by distillation.

In the present invention 3, for decreasing the residence time of the thermal treatment, an oxide of boron typified by orhtoboric acid, metaboric acid, tetraboric acid and boron oxide is added to the dehydration reactor. As an addition method, it may be introduced in the form of a solid, or it may be added in the form of an aqueous solution.

The oxide of boron converts a column bottom liquid to a liquid having a high boiling point to a great extent when it is concentrated in the column bottom liquid of a distillation column in a distillation step subsequent to the thermal treatment. The oxide of boron is therefore added in the smallest amount that is necessary for quality improvement.

That is, the oxide of boron is newly added in a weight ratio, based on the trimellitic acid, of 50 to 900 ppm, preferably 50 to 300 ppm.

The oxide of boron contained in the bottom liquid is inactivated and has little effect on the thermal treatment. The above weight ratio of the oxide of boron is a value including no oxide of boron in the bottom liquid of a distillation column which is circulated.

The residence time sufficient for converting the color component to a component having a high boiling point in the thermal treatment vessel is at least 5 minutes in the continuous method, and it is selected depending upon the thermal treatment temperature.

As described above, the thermal treatment is carried out so as to fully convert the color component to a component having a high boiling point, and then the distillation is carried out to obtain trimellitic acid anhydride. The distillation is carried out under reduced pressure of 50 torr or less. In the distillation, substances having a high boiling point are separated by simple distillation, while rectification distillation may be carried out for higher efficiency.

In the present invention 3, when part of the column bottom liquid of a distillation column is recycled to the thermal treatment vessel during the distillation, and a recycling operation is carried out, the concentration degree of the column bottom liquid of the distillation column in the distillation step after the thermal treatment is decreased, whereby the conversion of the column bottom liquid to a liquid having a high boiling point due to the oxide of boron can be prevented. When the column bottom liquid is recycled to the thermal treatment vessel, surprisingly, the oxide of boron contained in the column bottom liquid is inactivated, so that the conversion of the column bottom liquid to a liquid having a high boiling point can be inhibited, and the distillation can be carried out without any industrial problem. For preventing the conversion to a liquid having a high boiling point, the amount of the column bottom liquid that is to be recycled to the thermal treatment vessel is at least 10% by weight, preferably at least 20% by weight, based on the crude trimellitic acid.

The present invention 3 will be explained with reference to drawings. Figure shows one example of flow of the process for the production of trimellitic acid anhydride according to the present invention 3. Trimellitic acid obtained by oxidation of 1,2,4-aliphatic group substituted benzene, dialkylbenzaldehyde and/or their oxide intermediate is introduced into a dehydration reactor 2 through a line 1. In the dehydration reactor, the thermal dehydration under heat is carried out under atmospheric pressure to dehydrate the trimellitic acid. A mixture of trimellitic acid with trimellitic acid anhydride is introduced into a thermal treatment vessel 4 through a line 3. Further, an oxide of boron is introduced into the thermal treatment vessel through a line 5, and further, not only the dehydration but also the thermal treatment is carried but under reduced pressure to convert a color component to a component having a high boiling point.

The mixture of trimellitic acid and trimellitic acid anhydride from the thermal treatment vessel is introduced into a distillation column 7 through a line 6, and trimellitic acid anhydride having a high quality is distilled out and separated from a distillation column top through a line 8. Water formed by the dehydration is brought through a line 9 by gas to a vacuum pump. Substances having a high boiling point are withdrawn from a distillation column bottom through a line 10. Part of the bottom liquid of the distillation column is recycled to the thermal treatment vessel 4 through a line 11, which serves to avoid the problem caused by the conversion of the bottom liquid to a liquid having a high boiling point due to the concentration of the bottom liquid, and trimellitic acid anhydride having a high quality can be stably obtained.

According to the present invention 3, after the dehydration of crude trimellitic acid is nearly finished, the thermal treatment is carried out under reduced pressure in the presence of the oxide of boron in the smallest amount that is necessary, whereby a color component is converted to a component having a high boiling point. By purifying it by distillation, the hue of the trimellitic acid anhydride can be decreased, and at the same time, the purity of the trimellitic acid anhydride can be increased. Further, by recycling distillation column bottom liquid to the thermal treatment vessel, the conversion of the bottom liquid to a liquid having a high boiling point to a great extent can be prevented, and the distillation can be carried out without any industrial problem.

In the present invention 4, trimellitic acid obtained by oxidation in a liquid phase is dehydrated under heat such that the content of trimellitic acid in a mixture of trimellitic acid with trimellitic acid anhydride is 3% or less, preferably 0 to 1%.

However, it is very difficult to increase the dehydration ratio of trimellitic acid from the crude trimellitic acid as described above when the dehydration is carried out in one vessel under slightly reduced pressure or atmospheric pressure. It is therefore preferred to divide a dehydration reactor to at least two stages and increase the dehydration ratio stepwise.

For example, in a first dehydration reactor, the thermal dehydration under heat is carried out at a temperature of 200 to 300° C. under atmospheric pressure or a reduced pressure causing no influence on the operation, and in a second dehydration reactor, the dehydration is carried out under a reduced pressure of 200 torr or less, preferably 100 torr or less, whereby the content of trimellitic acid which is not dehydrated is adjusted to 3% or less.

In the second dehydration reactor (thermal treatment vessel), the thermal treatment is also carried out at the same time, whereby a color component is converted to a component having a high boiling point. As conditions of converting the color component to a component having a high boiling point, it is required to carry out thermal treatment at 250° C. or higher. The thermal treatment is preferably carried out in the range of from 250° C. to 300° C., and the higher the temperature is, the smaller the time period required for the thermal treatment is. However, when the temperature is higher than 300° C., the decomposition of trimellitic acid anhydride is no longer negligible. When the above thermal treatment is carried out under reduced pressure, the color component is converted to a component having a high boiling point, and it can be removed by distillation.

The present invention 4 has a characteristic feature in that the thermal treatment is carried out under reduced pressure for a long period of time without adding an oxide of boron to the thermal treatment vessel. The residence time of the thermal treatment is required to be at least 30 minutes in a continuous method, and it is selected depending upon the thermal treatment temperature.

The thermal treatment is carried out until a color component is fully converted to a component having a high boiling point, and the distillation is carried out, to obtain trimellitic acid anhydride. As a condition of the distillation, the distillation is carried out under a reduced pressure of 50 torr or less. In the distillation, substances having a high boiling point are separated by simple distillation, while rectification distillation may be carried out for higher efficiency.

According to the present invention 4, after the dehydration of crude trimellitic acid is nearly finished, the thermal treatment is carried out for a long time, to convert a color component to a component having a high boiling point, and it is purified by distillation, whereby the hue of the trimellitic acid anhydride can be decreased, the purity of the trimellitic acid anhydride can be increased, and the distillation can be carried out without any industrial problem.

In the above present inventions 3 and 4, the dehydration, the thermal treatment and the distillation can be carried out by any one of a batch method, a semi-batch method and a continuous method, while a continuous method is preferably used.

According to the process of the present invention, even trimellitic acid produced from a raw material having a low purity can be improved in quality, and trimellitic acid anhydride having a high quality can be stably produced.

DESCRIPTION OF THE PREFERRED EMBODIMENTS

The present invention will be specifically explained with reference to Examples hereinafter. The present invention shall not be limited by these Examples.

In Table 2, TMA stands for trimellitic acid. A yield refers to a product amount (molar ratio) of trimellitic acid or oxide intermediates (monocarboxylic acid, dicarboxylic acid) based on an aromatic aldehyde as a raw material. Examples 1 to 3 and Comparative Examples 1 (invention 1)

An autoclave made of titanium and equipped with a gas discharge tube having a reflux condenser, a gas introducing tube, a raw material continuous-feed pump and a stirrer was charged with 1,010 g of a catalyst solution which was prepared by mixing cobalt acetate tetrahydrate, manganese acetate tetrahydrate, a 47 wt % hydrogen bromide aqueous solution, glacial acetic acid and water, which had a cobalt concentration of 0.116% by weight, a manganese concentration of 0.117% by weight and a bromine concentration of 0.5% by weight and which had a water concentration changed, followed by feeding 134 g/h of 2,4-domethylbenzaldehyde and 808 g/h of a catalyst solution having the above concentrations. The reaction was carried out at a pressure of 32 kg/cm$^2$G at a temperature of 230° C. with an off-gas having an oxygen concentration of 2% by volume. A reaction product was continuously withdrawn so as to maintain a liquid surface at a constant level. The obtained reaction product was cooled to 30° C., and filtered to separate a crystal. The crystal was rinsed at 50° C. with acetic acid having the same weight as that of the crystal. The obtained crystal was dried, and the filtrate and the rinse liquid were analyzed to determine a yield and metals in the crystal. Table 1 shows the results.

TABLE 1

|  |  | Ex. 1 | Ex. 2 | Ex. 3 | CEx. 1 |
|---|---|---|---|---|---|
| Water content in solvent | wt % | 19 | 30 | 41 | 4 |
| Yield | mol % | 90.6 | 91.1 | 90.6 | 76.9 |
| Co in crystal | ppm | 470 | 140 | 15 | 5,290 |
| Mn in crystal | ppm | 580 | 160 | 14 | 6,030 |

Ex. = Example, CEx. = Comparative Example

Example 4

Example 2 was repeated except that 2,4-dimethylbenzaldehyde was replaced with 150 g/h of 2,4-dimethylbenzoic acid. The yield of an obtained crystal was 92.5 mol %. The content of cobalt in the crystal was 135 ppm, and the content of manganese in the crystal was 150 pm.

Example 5

Example 2 was repeated except that no cobalt was used, that the manganese concentration was changed to 0.057% by weight, that the bromine concentration was changed to 0.25% by weight and that a crystal separated by filtration was rinsed with water. The yield of an obtained trimellitic acid was 88.2 mol %, and the crystal had a manganese content of 4 ppm.

Example 6

Example 5 was repeated except that 2,4-dimethylbenzaldehyde was replaced with 150 g/h of 3,4-dimethylbenzoic acid. The yield of an obtained trimellitic acid was 89.2 mol %, and the crystal had a manganese content of 3 ppm.

Comparative Example 2

Example 5 was repeated except that the water concentration in the solvent was changed from 30% by weight to 8% by weight. The yield of an obtained trimellitic acid was 77.8 mol %, and the crystal had a manganese content of 3,750 ppm.

Example 7 (Invention 2)

A 2-liter autoclave made of titanium and equipped with a gas discharge tube having a reflux condenser, a gas introducing tube, a raw material continuous-feed pump and a stirrer was charged with 980 g of a catalyst solution which was prepared by mixing zirconium acetate, manganese acetate tetrahydrate, a 47 wt % hydrogen bromide aqueous solution, glacial acetic acid and water and which had a zirconium concentration of 0.01% by weight, a manganese concentration of 0.37% by weight and a bromine concentration of 0.4% by weight and a water concentration of 40% by weight, followed by feeding 182 g/h of 2,4-domethylbenzaldehyde and 703 g/h of a catalyst solution having the above concentrations. The reaction was carried out at a pressure of 25 kg/cm²G at a temperature of 200° C. with an off-gas having an oxygen concentration of 2% by volume. A reaction product was continuously withdrawn so as to maintain a liquid surface at a constant level. The residence time period was 60 minutes. The obtained reaction product was analyzed to determine a yield. Table 2 shows the results.

Example 8

Example 7 was repeated except that zirconium acetate was replaced with cerium acetate monohydrate and that the cerium concentration was 0.01% by weight. Table 2 shows the results.

Example 9

Example 7 was repeated except that zirconium acetate and cerium acetate monohydrate were used, that the zirconium concentration was 0.005% by weight and that the cerium concentration was 0.005% by weight. Table 2 shows the results.

Example 10

Example 7 was repeated except that zirconium acetate and cerium acetate monohydrate were used, that the zirconium concentration was 0.030% by weight, that the cerium concentration was arranged to be 0.030% by weight and that the manganese concentration was 0.32% by weight. Table 2 shows the results.

Comparative Example 3

Example 7 was repeated except that no zirconium was added and that the manganese concentration was 0.38% by weight. Table 2 shows the results.

Comparative Example 4

Example 7 was repeated except that zirconium acetate was replaced with cobalt acetate monohydrate and that the cobalt concentration was 0.01% by weight. Table 2 shows the results.

TABLE 2

|  | Ex. 7 | Ex. 8 | Ex. 9 | Ex. 10 | CEx. 3 | CEx. 4 |
|---|---|---|---|---|---|---|
| Concentrations of metal components in solvent (wt %) | | | | | | |
| Zr | 0.01 | 0 | 0.005 | 0.03 | 0 | 0 |
| Ce | 0 | 0.01 | 0.005 | 0.03 | 0 | 0 |
| Co | 0 | 0 | 0 | 0 | 0 | 0.01 |
| Mn | 0.37 | 0.37 | 0.37 | 0.32 | 0.38 | 0.37 |
| Yield (mol %) | | | | | | |
| TMA | 89.1 | 87.1 | 89.8 | 91.0 | 80.0 | 83.8 |
| Intermediate | 3.5 | 7.9 | 4.0 | 3.5 | 10.4 | 6.7 |

Ex.=Example, CEx.=Comparative Example

Example 11

Example 7 was repeated except that 2,4-dimethylbenzaldehyde was replaced with 2,4-dimethylbenzoic acid and that it was supplied at a rate of 203 g/h. The yield of an obtained trimellitic acid was 92.0 mol %, and the yield of an intermediate was 2.9 mol %.

Example 12

Example 7 was repeated except that 2,4-dimethylbenzaldehyde was replaced with 3,4-dimethylbenzaldehyde and that it was supplied at a rate of 182 g/h. The yield of an obtained trimellitic acid was 88.1 mol %, and the yield of an intermediate was 2.9 mol %.

Comparative Example 5 (Invention 3)

A crude trimellitic acid (trimellitic acid content 97.5%) obtained by oxidizing 2,4-dimethylbenzaldehyde according to the method described in JP-B-58-2222 was continuously supplied to a dehydration reactor at a rate of 165 parts per hour, and dehydrated under heat at 230° C. with a residence time period of 3 hours. The dehydration ratio of trimellitic acid from the dehydration reactor was 90%. Then, a mixture of trimellitic acid and trimellitic acid anhydride from the dehydration reactor was continuously supplied to a distillation column having theoretical two stages under a reduced pressure of 15 torr, and a column bottom liquid was continuously withdrawn at a rate of 3 parts per hour. The distillation column was operated at a reduced pressure of 15 torr, at a column top temperature of 250° C. and at a column bottom temperature of 250 to 260° C., and in a stabilized state, the temperature difference between the column top and the column bottom was 10° C. or less. Distilled trimellitic acid anhydride had a purity of 98.7%, a melting point of 167.3° C. and a melt color of APHA 120.

The melt color of the trimellitic acid anhydride was determined by melting it at 190° C. in atmosphere and comparing a melted trimellitic acid anhydride with a APHA standard liquid shown in JIS K1557-6.2.

Example 13

A thermal treatment vessel was placed between the dehydration reactor and the distillation column used in Comparative Example 5. The same procedure as that in Comparative Example 5 was carried out in the dehydration reactor. Then, a 10% boric acid aqueous solution was supplied to the thermal treatment vessel at a rate of 0.1 part per hour, and the boric acid concentration in the thermal vessel reached 60 ppm. Then, the dehydration and the thermal treatment were carried out under conditions of a reduced pressure of 50 torr, 260° C. and a residence time of 10 minutes. The dehydration ratio of trimellitic acid from the thermal treatment vessel was 99.4%. Then, a mixture of trimellitic acid and trimellitic acid anhydride from the thermal treatment vessel was continuously supplied to a distillation column having theoretical two stages, and a column bottom liquid was continuously withdrawn at a rate of 3 parts per hour. 20 Parts thereof was recycled to the thermal treatment vessel. The distillation column was operated at a reduced pressure of 15 torr, at a column top temperature of 250° C. and at a column bottom temperature of 250 to 260° C., and in a stabilized state, the temperature difference between the column top and the column bottom was 10° C. or less. Trimellitic acid anhydride distilled from the distillation column had a purity of 99.2%, a melting point of 167.4° C. and a melt color of APHA 80. The thermal treatment improved the trimellitic acid anhydride in product quality.

Comparative Example 6

A crude trimellitic acid (trimellitic acid content 96.1%) obtained by oxidizing a mixture containing 94% of 2,4-dimethylbenzoic acid, 1% of methylphthalic acid, 1% of methylphthalide and 4% of other impurities was continuously supplied to a dehydration reactor at a rate of 150 parts per hour, and dehydrated under heat under conditions of 500 torr, 235° C. and a residence time period of 3.5 hours. The dehydration ratio of trimellitic acid from the dehydration reactor was 92%. Then, a mixture containing trimellitic acid and trimellitic acid anhydride from the dehydration reactor was continuously supplied to a distillation column having theoretical four stages at a reduced pressure of 15 torr, and a column bottom liquid was continuously withdrawn at a rate of 3 parts per hour. In a stabilized state, the temperature difference between the column top and the column bottom was 10° C. or less. Distilled trimellitic acid anhydride had a purity of 98.6%, a melting point of 167.3° C. and a melt color of APHA 170.

Comparative Example 7

A thermal treatment vessel was placed between the dehydration reactor and the distillation column used in Comparative Example 6. The same procedure as that in Comparative Example 6 was carried out in the dehydration reactor. Then, a 10% boric acid aqueous solution was supplied to the thermal treatment vessel at a rate of 0.4 part per hour, and the boric acid concentration in the thermal treatment vessel reached 267 ppm, and the dehydration and the thermal treatment were carried out under conditions of a reduced pressure of 50 torr, 265° C. and a residence time of 50 minutes. The dehydration ratio of trimellitic acid from the thermal treatment vessel was 99.7%. Then, a mixture of trimellitic acid and trimellitic acid anhydride from the thermal treatment vessel was continuously supplied to a distillation column having theoretical four stages, and a column bottom liquid was continuously withdrawn at a rate of 3 parts per hour. The distillation column was operated at a reduced pressure of 15 torr and at a column top temperature of 250° C. As the bottom column liquid was concentrated, the column bottom temperature exceeded 280° C., and the temperature difference between the column top and the column bottom became 30° C. or more. It was therefore difficult to operate the distillation column. Distilled trimellitic acid anhydride had a purity of 99.2%, a melting point of 167.5° C. and a melt color of APHA 100. The thermal treatment improved the trimellitic acid anhydride in product quality.

Example 14

A thermal treatment vessel was placed between the dehydration reactor and the distillation column in the same manner as in Comparative Example 7. The same procedure as that in Comparative Example 7 was carried out in the dehydration reactor. Then, a 10% boric acid aqueous solution was supplied to the thermal treatment vessel at a rate of 0.4 part per hour, and the boric acid concentration in the thermal treatment vessel reached 267 ppm, and the dehydration and the thermal treatment were carried out under conditions of a reduced pressure of 50 torr, 265° C. and a residence time of 50 minutes. The dehydration ratio of trimellitic acid from the thermal treatment vessel was 99.7%. Then, a mixture of trimellitic acid and trimellitic acid anhydride from the thermal treatment vessel was continuously supplied to a distillation column having theoretical four stages, and a column bottom liquid was continuously withdrawn at a rate of 80 parts per hour and recycled to the thermal treatment vessel. Separately, further, 3 parts of a column bottom liquid was continuously withdrawn. The distillation column was operated at a reduced pressure of 15 torr and at a column top temperature of 250° C. and at a column bottom temperature of 250–260° C. In a stabilized state, the temperature difference between the column top and the column bottom was 15° C. or less. Trimellitic acid anhydride distilled from the distillation column had a purity of 99.2%, a melting point of 167.5° C. and a melt color of APHA 100. Even if the raw material had a low purity, trimellitic acid anhydride improved in product quality was obtained by the thermal treatment. Further, since the distillation column bottom liquid was recycled, the defect caused by the addition of boric acid was overcome, and the distillation was successfully carried out without any problem.

Example 15 (Invention 4)

A thermal treatment vessel was placed between the dehydration reactor and the distillation column used in Comparative Example 5. The same procedure as that in Comparative Example 5 was carried out in the dehydration reactor. Then, in the thermal treatment vessel, the dehydration and thermal treatment were carried out under conditions of a reduced pressure of 50 torr, 260° C. and a residence time of 1 hour. The dehydration ratio of trimellitic acid from the thermal treatment vessel was 99.5%. Then, the distillation was carried out in the same manner as in Comparative Example 5. Distilled trimellitic acid anhydride had a purity of 99.1%, a melting point of 167.4° C. and a melt color of APHA 80. The thermal treatment improved the trimellitic acid anhydride in product quality.

Comparative Example 8

A crude trimellitic acid (trimellitic acid content 96.1%) obtained by oxidizing a mixture containing 94% of 2,4-dimethylbenzoic acid, 1% of methylphthalic acid, 1% of methylphthalide and 4% of other impurities was continuously supplied to a dehydration reactor at a rate of 150 parts per hour, and dehydrated under heat under conditions of 500 torr, 235° C. and a residence time period of 3.5 hours. The dehydration ratio of trimellitic acid from the dehydration reactor was 92%.

Then, a mixture containing trimellitic acid and trimellitic acid anhydride from the dehydration reactor was continuously supplied to a distillation column having theoretical four stages at a reduced pressure of 15 torr. Distilled trimellitic acid anhydride had a purity of 98.6%, a melting point of 167.3° C. and a melt color of APHA 170.

Example 16

A thermal treatment vessel was placed between the dehydration reactor and the distillation column used in Comparative Example 8. The same procedure as that in Comparative Example 8 was carried out in the dehydration reactor. Then, in the thermal treatment vessel, the dehydration and the thermal treatment were carried out under conditions of a reduced pressure of 60 torr, 270° C. and a residence time of 4 hours. The dehydration ratio of trimellitic acid from the thermal treatment vessel was 99.7%.

Then, the distillation was carried out in the same manner as in Comparative Example 8. Trimellitic acid anhydride distilled from the distillation column had a purity of 99.2%, a melting point of 167.5° C. and a melt color of APHA 100. Even if the raw material had a low purity, trimellitic acid anhydride improved in product quality was obtained by the thermal treatment.

Comparative Example 9

A thermal treatment vessel was placed between the dehydration reactor and the distillation column used in Comparative Example 8. In the dehydration reactor, the same crude trimellitic acid as that used in Comparative Example 8 was continuously supplied at a rate of 150 parts per hour, and dehydrated under heat under conditions of 500 torr, 235° C. and a residence time of 3.5 hours. In the thermal treatment vessel, the dehydration and the thermal treatment were carried out under conditions of a reduced pressure of 500 torr, 270° C. and a residence time of 3 hours. The dehydration ratio of trimellitic acid from the thermal treatment vessel was 96.0%.

Then, the distillation was carried out in the same manner as in Comparative Example 8. Trimellitic acid anhydride distilled from the distillation column had a purity of 98.8%, a melting point of 167.3° C. and a melt color of APHA 160. It is seen that when the thermal treatment vessel has a low degree of reduced pressure and when the dehydration ratio is low, trimellitic acid anhydride is not improved in product quality even if the thermal treatment is carried out.

What is claimed is:

1. A process for the production of trimellitic acid, which comprises oxidizing a dialkyl aromatic aldehyde and/or its oxide derivative at 180 to 240° C. with an oxygen-containing gas in a lower aliphatic carboxylic acid solvent having a water content of 5 to 70% by weight in the presence of a catalyst containing a heavy metal and bromine.

2. A process according to claim 1, wherein the heavy metal includes manganese or a combination of manganese and cobalt.

3. A process according to claim 1, wherein the solvent has a bromide ion concentration of 0.05 to 2% by weight and a heavy metal atom concentration of 0.03 to 2% by weight, the heavy metal having an atomic ratio to the bromide ion in the range of from 0.5 to 10.

4. A process according to claim 1, wherein the oxidation is continuously carried out, and a mother liquor remaining after a trimellitic acid crystal is separated from an oxidation reaction mixture is recycled to an oxidation step.

5. A process according to claim 1, wherein the dialkyl aromatic aldehyde and/or its oxide derivative are/is at least one compound selected from 2,4-dimethylbenzaldehyde, 2,5-dimethylbenzaldehyde, 3,4-dimethylbenzaldehyde, 2,4-dimethylbenzoic acid, 2,5-dimethylbenzoic carboxylic acid or 3,4-dimethylbenzoic acid.

6. A process for the production of trimellitic acid, which comprises oxidizing a dialkyl aromatic aldehyde and/or its oxide derivative with an oxygen-containing gas at a temperature between 180° C. and 240° C. in a solvent containing a lower aliphatic carboxylic acid in the presence of a bromine-manganese based catalyst containing zirconium and/or cerium.

7. A process according to claim 6, wherein the lower aliphatic carboxylic acid solvent contains 5 to 70% by weight of water.

8. A process according to claim 6, wherein the solvent has a bromide ion concentration of 0.05 to 2% by weight and a concentration of total heavy metal atoms of zirconium, cerium and manganese in the range of from 0.03 to 2% by weight, the heavy metals having an atomic ratio to the bromide ion in the range of from 0.5 to 10.

9. A process according to claim 6, wherein the bromine-manganese based catalyst contains zirconium, cerium and manganese, and on the basis of a total amount of these metals, the catalyst has a zirconium content of 1 to 10% by weight, a cerium content of 1 to 20% by weight and a manganese content of 70 to 98% by weight.

10. A process according to claim 6, wherein the oxidation is carried out by a continuous method and a mother liquor remaining after a trimellitic acid crystal is separated from an oxidation reaction mixture is recycled to an oxidation step.

11. A process according to claim 6, wherein the dialkyl aromatic aldehyde and/or its oxide derivative are/is at least one compound selected from 2,4-dimethylbenzaldehyde, 2,5-dimethylbenzaldehyde, 3,4-dimethylbenzaldehyde, 2,4-dimethylbenzoic acid, 2,5-dimethylbenzoic acid or 3,4-dimethylbenzoic acid.

12. A process for the production of trimellitic acid anhydride from trimellitic acid obtained by oxidation of at least one member selected from the group consisting of 1,2,4-aliphatic-groups-substituted benzene, dialkylbenzaldehyde and oxide intermediate thereof, which process comprises thermally treating a crude trimellitic acid or a mixture of trimellitic acid with trimellitic acid anhydride, obtained by dehydration of the trimellitic acid under heating, together with boron oxide under reduced pressure, then introducing a thermally treated product into a distillation column, and continuously recycling part of a bottom liquid in the distillation column to the step of the thermal treatment.

13. A process according to claim 12, wherein the thermal treatment is carried out under a reduced pressure of 200 torr or less, at a temperature of at least 250° C. for a treatment time of at least 5 minutes.

14. A process according to claim 12, wherein the mixture of trimellitic acid with trimellitic acid anhydride has a trimellitic acid content of 3% by weight or less.

15. A process according to claim 12, wherein an oxide of boron is added in an amount of 50 to 900 ppm based on the crude trimellitic acid.

16. A process according to claim 12, wherein the bottom liquid is recycled from the distillation column in an amount of at least 10% by weight based on the trimellitic acid and the trimellitic acid anhydride to be thermally treated.

17. A process according to claim 12, wherein the oxide of boron is at least compound selected from orthoboric acid, metabroic acid, tetraboric acid or boron oxide.

18. A process for the production of trimellitic acid anhydride from crude trimellitic acid obtained by oxidation of at least one member selected from the group consisting of 1,2,4-aliphatic-groups-substituted benzene, dialkylbenzaldehyde and an oxide intermediate thereof, which process comprises thermally treating the crude trimellitic acid or a mixture of trimellitic acid with trimellitic acid anhydride, obtained by dehydration of the crude trimellitic acid under heating, until the amount of trimellitic acid based on the total amount of trimellitic acid and trimellitic acid anhydride is 3% by weight or less, and introducing the thermally treated product into a distillation column.

19. A process according to claim 18, wherein the thermal treatment is carried out under a reduced pressure of 200 torr or less, at a temperature of at least 250° C. for a treatment time of at least 30 minutes.

* * * * *